| United States Patent [19] | [11] | 4,131,612 |
|---|---|---|
| Uchiyama | [45] | Dec. 26, 1978 |

[54] PROCESS FOR PURIFYING CRUDE DIBENZYLIDENE SORBITOL

[75] Inventor: Hiroshi Uchiyama, Hirakata, Japan

[73] Assignees: E. C. Chemical Ind. Co., Ltd.; C. Itoh & Co., both of Japan

[21] Appl. No.: 795,185

[22] Filed: May 9, 1977

[30] Foreign Application Priority Data

Jul. 1, 1976 [JP] Japan .................................. 51-77128

[51] Int. Cl.$^2$ .................. C07D 319/04; C07D 317/10
[52] U.S. Cl. ............................ 260/340.7; 260/340.9 R
[58] Field of Search ....................... 260/340.7, 340.9 R

[56] References Cited

U.S. PATENT DOCUMENTS

| 3,721,682 | 3/1973 | Murai et al. | 260/340.7 |
| 3,853,917 | 12/1974 | Okada et al. | 260/340.7 |
| 3,855,227 | 12/1974 | Hollander et al. | 260/340.7 |

*Primary Examiner*—Ethel G. Love
*Attorney, Agent, or Firm*—Wenderoth, Lind & Ponack

[57] ABSTRACT

Purified dibenzylidene sorbitol is prepared by mixing crude dibenzylidene sorbitol containing monobenzylidene sorbitol and tribenzylidene sorbitol as by-product impurities with a lower aliphatic alcohol to dissolve the impurities, and separating and recovering the undissolved dibenzylidene sorbitol. This process affords dibenzylidene sorbitol having a purity of at least 98% from crude dibenzylidene sorbitol with a purity of about 95%.

2 Claims, No Drawings

PROCESS FOR PURIFYING CRUDE DIBENZYLIDENE SORBITOL

This invention relates to a process for purifying crude dibenzylidene sorbitol.

Dibenzylidene sorbitol is known as a gelling agent for organic liquids. It is prepared usually by reacting 1 mole of d-sorbitol with 2 moles of benzaldehyde in water or a certain organic liquid as a reaction medium in the presence of an acid catalyst at an elevated temperature thereby to perform dehydrocondensation (U.S. Patent 3,721,682). The dibenzylidene sorbitol formed by this reaction contains 2 to 5% by weight, or a larger amount, up to about 7% by weight, of by-product monobenzylidene sorbitol and tribenzylidene sorbitol. Sometimes, it contains traces of unidentifiable colored impurities.

Recently, utility has been developed to use dibenzylidene sorbitol as a flocculating agent (U.S. Patent 3,872,000) or a modifier for polyolefin resins (U.S. Patent 4,016,118). For these uses, the presence of the aforesaid by-products sometimes gives undesirable results, and it is desired to use purified dibenzylidene sorbitol free from these by-products.

Dibenzylidene sorbitol is soluble in N-methyl-2pyrrolidone and dimethyl formamide, and can be purified by recrystallization from these solvents. However, since these solvents have a high boiling point, long periods of time are required for drying the crystals obtained. Moreover, these solvents are expensive.

It is an object of this invention therefore to provide a process which can easily remove monobenzylidene sorbitol and tribenzylidene sorbitol from crude dibenzylidene sorbitol.

The above object can be achieved in accordance with this invention by a process for purifying crude dibenzylidene sorbitol, which comprises mixing 1 part by weight of crude dibenzylidene sorbitol obtained by reacting 1 mole of d-sorbitol with 2 moles of benzaldehyde and containing not more than about 7% by weight of by-product monobenzylidene sorbitol, tribenzylidene sorbitol, or both as impurities, with 5 to 15 parts by weight of at least one lower aliphatic alcohol at a temperature of at least 50° C. but below the boiling point of the lower aliphatic alcohol, thereby to dissolved the impurities in the aliphatic alcohol, and then separating and recovering the purified dibenzylidene sorbitol from the resulting solution.

Examples of the lower aliphatic alcohol that can be used in the present invention are methyl alcohol, ethyl alcohol, isopropyl alcohol, and mixtures of at least two of these.

The process of the invention can be conveniently performed by mixing 1 part by weight of the crude dibenzylidene sorbitol with 5 to 15 parts by weight, preferably 7 to 12 parts by weight, of the lower aliphatic alcohol in a vessel, heating the mixture at a temperature of at least 50° C., preferably at least 60° C., but below the boiling point of the lower aliphatic alcohol, maintaining the mixture at this temperature for 1 minute to 1 hour, preferably 20 to 40 minutes, and then separating the purified dibenzylidene sorbitol from the solution by filtration while maintaining it at this temperature, and drying the dibenzylidene sorbitol separated.

Preferably, the heating of the mixture is done in a vessel equipped with a reflux condenser to a temperature near the boiling point of the lower aliphatic alcohol, for example, 60 to 63° C. for methyl alcohol, 75 to 78° C. for ethyl alcohol, and 80 to 83° C. for isopropyl alcohol, while stirring the mixture.

As a result of the aforesaid treatment with the lower aliphatic alcohol, the monobenzylidene sorbitol and tribenzylidene sorbitol dissolve in the lower aliphatic alcohol, and are removed from dibenzylidene sorbitol which does not substantially dissolve in it. The amount of the dibenzylidene sorbitol which may be dissolved in the alcohol is very small.

Traces of by-product colored impurities contained in the dibenzylidene sorbitol together with mono- and tri-benzylidene sorbitols also dissolve in the lower aliphatic alcohol, and are removed.

The solubilities of the various by-products contained in the crude dibenzylidene sorbitol in lower aliphatic alcohol are as shown in the following Table 1 according to the present inventor's measurement Table 1

|  | Solvent | |
| --- | --- | --- |
|  | Methyl alcohol (63° C) | Ethyl alcohol (78° C) |
| Dibenzylidene sorbitol | 0.7 g | 1 g |
| Tribenzylidene sorbitol | 1.9 g | 3 g |
| Monobenzylidene sorbitol | More than 20g | More than 20g |
| Unidentifiable by-product colored substances | Completely dissolved | Completely dissolved |

In the above table, the weight of each substance dissolved per 100 g of the solvent is expressed in grams.

The process of this invention can also be performed by pouring the heated lower aliphatic alcohol over the crude dibenzylidene sorbitol.

The filtrate of the lower aliphatic alcohol having dissolved in it the impurities and a small amount of dibenzylidene sorbitol is cooled to precipitate dibenzylidene sorbitol. The residue is then press-filtered to precipitate mono- and tribenzylide sorbitols from the filtrate, thereby to recover the solvent for reuse.

The process of this invention illustrated hereinabove makes it possible to recover dibenzylidene sorbitol having a purity of at least 98%, preferably at least 99%, from crude dibenzylidene sorbitol which contains up to about 7% by weight, preferably up to 5% by weight, of monobenzylidene sorbitol, tribenzylidene sorbitol, or both and sometimes, colored by-products.

The resulting high-purity dibenzylidene sorbitol is a white powder having nacreous luster with a specific gravity of less than 0.12 and a melting point of 210 ± 2° C. Recrystallization of the purified dibenzylidene sorbitol can increase the purity to at least 99.9%.

The following Examples further illustrate the present invention.

EXAMPLE 1

(A) Preparation of crude dibenzylidene sorbitol

A reactor equipped with a decanter-fitted condenser, a thermometer, a gas introducing inlet and a stirrer was charged with 64 g of a 70% aqueous solution of sorbitol, 53 g of benzaldehyde and 500 ml of cyclohexane. The inside of the reactor was purged with nitrogen gas. While thoroughly mixing the materials in the reactor, 3 g of conc. sulfuric acid was gradually added. Then, the temperature of the mixture in the reactor was raised to 70 to 80° C. (the temperature at which water and cyclohexane form an azeotrope). With the progress of the reaction, the water in the mixture within the reactor and the water formed by condensation were withdrawn from the reactor through the decanter-fitted condenser as an azeotrope with cyclohexane. When this operation was continued for about 5 hours, the water in the reaction mixture was completely removed, and the reaction ended.

The reaction mixture remaining in the reactor was cooled to room temperature. The resulting slurry was neutralized, washed with water, and filtered to remove the acid in the reaction mixture. The residue was washed several times with hot water, and dried to afford 64 g of a pearl-like white solid powder of crude dibenzylidene sorbitol. Each 100 g of the crude benzylidene sorbitol contained about 4.3 g of monobenzylidene sobitol and tribenzylidene sorbitol combined.

(B) Purification of crude benzylidene sorbitol

A 5-liter enamelled beaker equipped with a reflux condenser was kept in a warm water bath, and 100 g of the crude dibenzylidene sorbitol obtained by the procedure of (A) above and 900 g of methyl alcohol were placed in the beaker. The mixture was slightly boiled by heating it to a temperature between 60 and 70° C., and maintained for 40 minutes. The slurry-like mixture was then separated by filtration using a filter press, washed with cold methanol, and dried, thereby to afford 96 g of purified dibenzylidene sorbitol as a powder having a beautiful nacreous luster.

The purities and properties of the crude and purified dibenzylidene sorbitols are shown in Table 2.

Table 2

|  | Purity(%) | Color* | Bulk density** | Melting point (° C) |
|---|---|---|---|---|
| Crude | 95.7 | 140 | 0.230 | 205 |
| Purified | 99.8 | 35 | 0.084 | 210 |

*A 15% dimethylformamide solution of the sample was tested for color by the method of Americal Public Health Association.
**The sample was placed in a test tube, and let fall onto a desk from a height of 3 cm ten times, and the mass of the sample per unit volume was determined.

EXAMPLE 2

The procedure of Example 1 was repeated except that 95% ethyl alcohol was used instead of the methyl alcohol, and the mixture was maintained at a temperature of 70° C. for 30 minutes. There was obtained 96 g of purified dibenzylidene sorbitol having a purity of 99.8%, a color of 35, a bulk density of 0.088, and a melting point of 209.8° C.

EXAMPLE 3

The procedure of Example 1 was repeated except that isopropyl alcohol was used instead of the methyl alcohol, and the mixture was maintained at 80 to 90° C. for 40 minutes. There was obtained 95 g of purified dibenzylidene sorbitol having a purity of 99.5%, a color of 36, a bulk density of 0.095 and a melting point of 210° C.

What is claimed is:

1. A process for purifying crude dibenzylidene sorbitol, which comprises mixing 1 part by weight of crude dibenzylidene sorbitol obtained by reacting 1 mole of d-sorbitol with 2 moles of benzaldehyde and containing not more than about 7% by weight of by-product monobenzylidene sorbitol, tribenzylidene sorbitol, or both as impurities, with 5 to 15 parts by weight of at least one lower aliphatic alcohol at a temperature of at least 50° C. but below the boiling point of the lower aliphatic alcohol, thereby to dissolve the impurities in the aliphatic alcohol, and then separating and recovering the purified dibenzylidene sorbitol from the resulting solution.

2. The process of claim 1 wherein the lower aliphatic alcohol is selected from the group consisting of methyl alcohol, ethyl alcohol and isopropyl alcohol.

* * * * *